United States Patent [19]

Angstadt et al.

[11] 4,022,841

[45] May 10, 1977

[54] ORGANOMETALLIC COMPLEXES AS ALKYLAROMATIC OXIDATION CATALYSTS

[75] Inventors: Howard P. Angstadt, Media; William P. Griffin, Jr., Bethel Park, both of Pa.

[73] Assignee: Sun Company, Inc., Philadelphia, Pa.

[22] Filed: Oct. 31, 1968

[21] Appl. No.: 772,421

Related U.S. Application Data

[63] Continuation-in-part of Ser. No. 741,285, July 1, 1968, abandoned, which is a continuation-in-part of Ser. No. 695,312, Dec. 26, 1967, abandoned.

[52] U.S. Cl. .................... 260/610 B; 252/431 P
[51] Int. Cl.² ............... C07C 179/02; C07C 179/04
[58] Field of Search ........... 260/610 B, 638 P, 610, 260/610 R

[56] References Cited

UNITED STATES PATENTS 3,270,084  8/1966  Schrieshelm .................. 260/683.2

FOREIGN PATENTS OR APPLICATIONS 745,128  2/1956  United Kingdom ........... 260/610 B

*Primary Examiner*—James O. Thomas, Jr.
*Assistant Examiner*—W. B. Lone
*Attorney, Agent, or Firm*—J. Edward Hess; Donald R. Johnson; Stanford M. Back

[57] ABSTRACT

Organometallic complexes formed between hexaalkylphosphoramides (HAPA) and metal salts, including rare earth metals, have been found to be effective catalyst for the oxidation of secondary and tertiary alkylaromatics to form valuable oxidation products, particularly the corresponding hydroperoxides. Novel complexes formed between HAPA and metal salts of the lanthanide series have been found to be especially effective in the selective formation of the hydroperoxides at high conversion rates. By substantially increasing the agitation and/or aeration of the reaction medium it is possible to increase these high conversion rates still further.

16 Claims, No Drawings

ORGANOMETALLIC COMPLEXES AS ALKYLAROMATIC OXIDATION CATALYSTS

CROSS-REFERENCE TO RELATED APPLICATIONS

This application is a continuatin-in-part of U.S. Ser. No. 741,285 filed July 1, 1968 now abandoned, which in turn is a continuation-in-part of U.S. Ser. No. 695,312 filed Dec. 26, 1967, now abandoned.

BACKGROUND OF THE INVENTION

This invention relates to a novel process for the oxidation of secondary and tertiary alkylaromatic hydrocarbons such as cumene, ethylbenzene, sec.-butylnaphthalene and the like to form the corresponding oxidation products, such as alcohols, aldehydes, ketones, hydroperoxides, and the like. The invention also relates to certain novel organometallic complexes useful as oxidation catalysts in this process. More particularly, this invention is directed to the use of complexes formed by reacting metal salts with a hexaalkylphosphoramide (hereinafter HAPA) as oxidation catalysts in the aforesaid process, and especially those complexes formed between HAPA and lanthanide metal salts.

The oxidation of the alkyl side chains of aromatic compounds is already well known in the art. Thus, for example, it is known that tertiary alkylaromatics such as cumene can be auto-oxidized very slowly to form cumyl hydroperoxide when air or oxygen is rapidly passed through cumene warmed to about 80° C. Also, Canadian Pat. No. 510,517 teaches that the rate of oxidation of cumene can be enhanced when carried out in the presence of alkali or alkaline earth metal oxides of hydroxides, or in the presence of salts and oxides of heavy metals. Under these conditions, the conversion rate is only 2–3 percent per hour. Other alkylaromatic oxidation catalysts are likewise well known, but in most instances, again, the conversion rate is low, as is the overall yield of the desired oxidation product.

It is an object of this invention, therefore, to provide a novel process for the oxidation of secondary and tertiary alkylaromatic compounds whereby the oxidation rate, or the selectivity, or both, may be increased, particularly with respect to the formation of the corresponding hydroperoxides.

It is a further object of this invention to provide certain novel organometallic complexes useful as catalysts in the oxidation process.

SUMMARY OF THE INVENTION

It has now been found, in accordance with the present invention, that organometallic complexes formed between metal salts, preferably those derived from transition metals, (including metals of the lanthanide and actinide series), and hexaalkylphosphoramides are effective catalysts in the oxidation of secondary and tertiary alkylaromatic hydrocarbons. Certain of these catalysts, and particularly those derived from metal salts of the lanthanide series, are especially effective in forming the hydroperoxides of the alkylaromatic hydrocarbons to the exclusion of other hydrocarbon oxidation products, thus providing the hydroperoxides in high yields at increased conversion rates. Throughout this description it will be understood that the term "lanthanide series" is meant to include the metal lanthanum itself as well.

It has also been found, in accordance with this invention, that the conversion rates can be even further enhanced if the agitation and/or aeration of the reaction medium is significantly increased beyond the conventional mixing techniques.

DESCRIPTION OF THE INVENTION

The organometallic catalysts employed in the process of this invention, namely, the metal salt . HAPA complexes, may be represented by the general formula:

$$MX_n(HAPA)_m$$

where M is a metal cation, preferably a transition metal from groups IIIB, IVB, VB, VIB, VIIB, VIIIB, IB, IIA or IIB of the periodic table, including the lanthanides and actinides; HAPA is a hexaalkylphosphoramide having the formula:

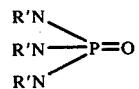

wherein R' is an alkyl group of from 1 to 30 carbon atoms, and preferably a $C_1$–$C_4$ radical; X is the anion of the metal salt, m is an integer of from 1 to 8; and n is an integer from 1 to 4. These complexes may be prepared in accordance with the teachings of Inorganic Chemistry, I, 866–872 (1962) wherein is described the complexing of hexamethylphosphoramide (HMPA) with the perchlorate salts of zinc, cobalt, and nickel. Briefly, the preparation of these compounds may readily be achieved by mixing a hydrate of the metal salt with an excess of an HAPA and recovering the resultant crystals in a known manner. Alternatively, the complex may be prepared by first dissolving the metal salt in an excess of solvent, preferably an alkanol such as t-butanol, to which solution is added an excess of HAPA, followed by routine recovery and drying of the resulting precipitate. In some instances the complex does not form a solid which can be recovered readily, if at all, in which case the resulting solution may satisfactorily be employed instead. These organometallic complexes may be employed either as the purified solid or in solution with excess HAPA itself as the preferred solvent therefor.

The metal salts used in forming the organometallic complexes are, as stated above, any metals of the periodic table, and preferably those derived from transition metals of groups IIIB, IVB, VB, VIB, VIIB, VIIIB, IB, IIA and IIB including the lanthanide and actinide metals. The anions of these salts may be any inorganic group, although the chlorides, bromides, nitrates, carbonates and perchlorates are generally preferred.

As also mentioned hereinabove, the oxidation products of the instant process are generally, alcohols, aldehydes, ketones, hydroperoxides, or mixtures thereof. Of these various products, maximization of the formation of the hydroperoxides is generally preferred inasmuch as these compounds are especially useful as intermediates in the preparation of such products as phenols, naphthols, acetone, and the like. Accordingly, as a preferred embodiment of this invention, it has been discovered that certain of the various metals, including the following, are particularly effective as catalysts in the preparation of hydroperoxides from secondary and tertiary alkylaromatic compounds, namely, dysprosium, erbium, praseodymium, nickel, titanium, thorium, neodymium, lead, ferrous iron, bismuth, zinc and cerium. These metals preferentially give yields of over 90 percent hydroperoxides to the exclusion of other oxidation products at conversion rates of at least about 4 percent per hour, and in many cases as high as 20 to 25 percent per hour. In the case of those remaining metals which yield lesser amounts or no hydroperoxides in the final product, while applicants do not wish to be bound by any particular theory, it is believed that they too yield hydroperoxides which are then rapidly decomposed by the catalyst complex to form aldehydes, ketones and the like.

It has further been determined, in accordance with this invention, that the anion, as well as the particular metal, can affect the percentage yield of hydroperoxide and its rate of conversion. For example, when cumene is oxidized in the presence of $MnBr_2 \cdot 2HMPA$, some cumyl hydroperoxide is found amongst the oxidation products, while $MnCl_2 \cdot 2HMPA$, on the other hand, yields greater amounts of cumyl hydroperoxide, while $MN(ClO_4)_2 \cdot 4$ HMPA gives exclusively the hydroperoxide. It will be understood, of course, that this illustration is not meant to be exclusive of other anions whose activity may likewise vary the hydroperoxide conversion rate depending upon the metal and the substrate employed.

The secondary and tertiary alkylaromatic hydrocarbons employed as the starting materials in this process include compounds having the structural formula

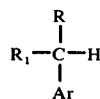

wherein R is lower alkyl; $R_1$ is lower alkyl or hydrogen; Ar is a substituted or unsubstituted aromatic nucleus such as phenyl or naphthyl; and wherein R and $R_1$ may be the same or different alkyl groups. The alkyl groups may contain from 1 to 10 carbon atoms, and are preferably those containing from 1 to 4 carbon atoms. The aromatic nucleus may be substituted by such groups as lower alkyl, lower alkoxy, halo, nitro, or cyano radicals. Preferably, the secondary or tertiary alkylaromatic hydrocarbon is represented by such compounds as cumene, ethylbenzene, or sec.-butylnaphthalene, although it is understood that compounds such as n-butylbenzene, sec.-butylbenzene, isopropylnaphthalene and the like may also be employed.

The process of this invention is conveniently carried out by the rapid passage of air or oxygen through a suitable reactor, to which has first been added a solution of the alkylaromatic hydrocarbon and organometallic catalyst. The solvent for the reaction is preferbly an excess amount of the alkyl aromatic starting material, although other solvents which are inert to the reaction of peroxidation may likewise be employed. The air or oxygen should desirably be brought into intimate contact with the liquid phase, for example, by the use of high speed stirrers, suitable nozzles or the like.

The amount of catalyst employed will vary depending upon the nature and amount of material to be oxidized and the particular catalyst employed. In general, however, from about 0.1 to 5.0 parts by weight of catalyst per 100 parts of substrate, and preferably from 0.5 to 1.5 parts per 100 parts has been found to be satisfactory.

The rate of input of oxygen or air will likewise vary depending upon the reaction temperature and pressure employed. There should be provided an amount at least theoretically sufficient to convert the alkyl aromatic compound to the corresponding hydroperoxide, and preferably an excess of this amount. In general, a flow rate ranging from 0.5 to 300 liters per hour is sufficient for most conversions, depending upon other reaction conditions described in more detail below. While the reaction is preferably carried out at atmospheric pressure, it is possible to employ an oxygen pressure of from about 2 atmospheres to 50 atmospheres, and preferably about 1 to 10 atmospheres. At these higher pressures the oxidation rate is found to increase substantially when the organometallic complexes are employed, and particularly those catalysts which are selective for hydroperoxide formation.

The reaction temperature may range from about 80° to 150° C, and preferably from 90° to 120° C. At temperatures above 150° C the catalysts tend to be thermally unstable.

The reaction is generally run for from half an hour to 10 hours, depending upon the amount of substrate employed and the degree of conversion desired. When, however, a hydroperoxide is the principal product being formed, it is desirable that the reaction be terminated after a period of 1 to 6 hours at which point the reaction rate usually begins to taper off.

Advantageously, when the principal product is a hydroperoxide, small amounts of the hydroperoxide corresponding to the desired product may be introduced into the reaction medium to act as a reaction initiator. Thus, for example, when cumene is being oxidized, it has been found to be advantageous to add small amounts of cumyl hydroperoxide in order to further accelerate the initial rate of reaction. The amount of hydroperoxide to be added is not critical, but 0.1 to to 1.0% by weight of the starting material is preferred.

The resulting products are readily recovered from the reaction medium by conventional methods. Thus, for example, an hydroperoxide may be conveniently recovered by isolating it as its sodium salt by addition of concentrated aqueous NaOH to the reaction product, followed by separation and drying of the hydroperoxide salt.

The aldehyde, ketone and hydroperoxide products formed by this process are well known commercially useful products. Thus, when cumene is oxidized to form cumyl hydroperoxide, this material, when reacted with an inorganic acid such as sulfuric acid, forms phenol and acetone.

In a preferred embodiment of this invention it has been found that the rate of oxidation achieved by the catalysts of this invention can be improved still further if the reaction medium is vigorously agitated beyond the degree of agitation normally achieved by conventional techniques. This agitation may be effected either by mechanical means or by vigorously bubbling air or oxygen through the reaction medium.

Mechanical agitation has been found to be particularly effective in those cases where the rate at which the oxygenating gas is introduced into the reactor is low, i.e., below about 3 liters per hour. Thus, for example, when air is merely introduced at the surface of the reaction mixture, agitation by a commercially available reciprocating disc type stirrer (e.g., "Vibro-Mixer," Chemapec, Inc., Hoboken, N.J.) has been found to increase the rate of oxidation per hour by as much as four-fold.

Alternatively, these increased rates may similarly be achieved, and mechanical agitation substantially or entirely dispensed with by appreciably increasing the rate at which air or oxygen is introduced into the reaction medium. This is preferably accomplished by bubbling the oxygenating gas through the reaction mixture vigorously, desirably in such a manner as to insure maximum dispersal of the gas through the medium, as for example, by using fritted glass discs or the like. Depending upon the amount of liquid medium involved, the rate of oxygenating gas may generally vary from about 3 to 300 liters per hour.

In the following examples, unless otherwise noted, both rate of conversion of the starting material and selectivity of the catalyst for converting the starting material to the corresponding hydroperoxide were measured. To measure rate of conversion, regardless of the nature of the oxidation product, the amount of oxygen uptake in a closed system was used as measure of the amount of oxidation which took place; to measure the amount of hydroperoxide formed, samples of the reaction medium were periodically withdrawn and iodometrically titrated to determine the hydroperoxide content. On the basis of both of these figures the selectivity of any given catalyst for the formation of hydroperoxide could then be routinely determined.

EXAMPLE 1

The metal salt.HAPA catalyst of the present invention may be prepared in accordance with either of the following two methods, wherein the lanthanide metal salts and hexamethylphosphoramide (HMPA) are used by way of illustration:

A. Neodymium chloride hydrate (2 g.) was warmed in a test tube with a 5 molar excess of HMPA. The warming was continued until all of the salt was in solution. Upon cooling, a light purple substance crystallized, filtered out and dried on a clay plate. This substance analyzed correctly for carbon and hydrogen for a compound of the formula $NdCl_3 \cdot 3HMPA \cdot XH_2O$ where X is one or two. The infrared spectra showed a P=O absorption displaced from 1210 $cm^{-1}$ to 1180$^{-1}$ in agreement with the existing literature data.

In accordance with the foregoing procedure, but substituting $HoCl_3$ and $DyCl_3$ for $NdCl_3$ there was obtained the corresponding $HoCl_3 \cdot 3HMPA$ and $DyCl_3 \cdot 3HMPA$, respectively.

B. $ErCl_3$ (2 g.) was dissolved in 5 cc. of n-butanol, and to this solution as added an excess of HMPA. The resulting crystals were filtered and dried to recover $ErCl_3 \cdot HMPA$.

This procedure is particularly useful where no solid complx is formed, in which case the n-butanol can be removed by evaporation under a stream of nitrogen and the resulting solution containing the metal salt-HAPA complex in excess HAPA can be used as the catalyst.

Alternatively, one can dissolve the hydrated metal salts in an excess of 2,2-dimethoxypropane to obtain a solution of the anhydrous salt in acetone and methanol. By adding an HAPA to this solution and evaporating this solvent under nitrogen, one obtains as a crystalline residue the anhydrous metal salt HAPA complex. Thus, for example, in accordance with the foregoing procedure, but substituting $PrCl_3$ and $SmCl_3$ for $ErCl_3$ there was obtained the corresponding $PrCl_3 \cdot HMPA$ and $SmCl_3 \cdot HMPA$, respectively.

By employing either of the foregoing procedures, but substituting other metal salts, as desired, for those employed above, additional catalyst complexes useful in the process of the present invention may likewise be routinely prepared.

EXAMPLE 2

The usefulness and effectiveness of the metal salt-.HAPA catalyst complexes was demonstrated in a series of reactions wherein cumene was oxidized in the presence of catalysts prepared from HMPA and a variety of metal salts. In each of the following runs a standard reaction consisted of combining 12.0 g. (0.1 moles) of cumene, approximately 0.1 mole percent of catalyst complex (about 60 mg.), and 0.2 cc. of cumene hydroperoxide in a 50 ml. Morton flask. The flask was immersed in an oil bath at 100° C, stirring with a magnetic stirring bar was started, and the flask then opened to an oxygen-containing buret. In those instances where the complex was isolated as a solid, about 60 mg. was used; in all other instances, unless otherwise noted, a solution of the metal complex in excess HMPA was employed. Both oxygen uptake, its measure, the conversion rate, and hydroperoxide content were periodically noted. The results obtained are reported in Table I as follows:

TABLE I

| | | CONVERSION AND HYDROPEROXIDE YIELD DATA | | | | | | | YIELD |
|---|---|---|---|---|---|---|---|---|---|
| RUN | HMPA COMPLEXED WITH: | % CONVERSION BY OXYGEN UPTAKE | | | | | | % ROOH* | % of ROOH |
| | | 1 hr. | 2 hrs. | 3 hrs. | 4 hrs. | 5 hrs. | 6 hrs. | | |
| 1. | $NiCl_2$ | 6.04 | 10.4 | 14.5 | 17.8 | | | 16.8 | 94 |
| 2. | $CuCl_2$ | 3.6 | 4.9 | | | | | 1.7 | 24 |
| 3. | $CoCl_2$ | | 7.6 | | | | | 2.2 | 29 |
| 4. | $CrCl_3 \cdot 6H_2O$ | 4.6 | 7.5 | | | | | 2.7 | 36 |
| 5. | $TiCl_4$ | | | | 16.3 | | 19.8 | 18.8 | 95 |
| | | | | | 14.0 | | 16.3 | 15.4 | 94 |
| 6. | $VCl_3$ | | 5.0 | 6.1 | | | | 1.3 | 21 |
| 7. | $MnCl_2 \cdot 4H_2O$ | 6.7 | 11.0 | | | | | 1.5 | 14 |
| 8. | $AgNO_3$ | | 1.6 | | | | | 1.5 | 94 |
| 9. | $ThO_2$ | | 5.0 | | 9.5 | | 12.7 | 14.4 | 100+ |
| 10. | $PdCl_2$ | 2.9 | 5.4 | | | | | 6.6 | >100 |
| 11. | $O_5Cl_4$ | | 2.5 | 5.2 | 7.9 | | | 5.3 | 67 |
| 12. | $NdCl_3$ | 4.1** | 7.8** | 12.0** | 17.4** | | | 26.7(7 hrs.) | |
| | | 4.3 | 8.5 | 12.0 | | | | 13.4 | >100 |
| 13. | $PbCl_2$ | 2.6 | | 4.5 | 5.7 | 7.0 | | 9.6 | >100 |
| 14. | $ZnCl_2$ | 5.0 | 8.0 | 10.0 | | | | 11 | >100 |
| 15. | $Cu_2Cl_2$ | 3.9 | 5.6 | | | | | <0 | 0 |
| 16. | $Ce(NO_3)_4$ | 5.1 | 8.4 | 10.6 | 12.2 | | | 6.0 | 49 |
| 17. | $FeCl_3$ | 4.1 | 6.0 | | | | | 3.4 | 57 |
| 18. | $FeCl_2$ | 4.6 | 8.2 | 10.6 | | | | 9.8 | 92 |

TABLE I-continued

CONVERSION AND HYDROPEROXIDE YIELD DATA

| RUN | HMPA COM-PLEXED WITH: | % CONVERSION BY OXYGEN UPTAKE | | | | | | % ROOH* | YIELD % of ROOH |
|---|---|---|---|---|---|---|---|---|---|
| | | 1 hr. | 2 hrs. | 3 hrs. | 4 hrs. | 5 hrs. | 6 hrs. | | |
| 19. | BiCl$_3$ | 4.3 | 7.7 | 10.9 | 11.9 | 13.2 | | 12.7 | 96 |
| 20. | HMPA alone | 0.5 | 1.1 | 1.6 | | | | | |
| 21. | No Catalyst | 0.2 | 0.7 | 1.5 | 2.2 | | 4.8 | 2.0 | 91 |

*Value given for longest time cited in prior columns.
+Value for four hour sample.
**Values for this run are all by hydroperoxide (ROOH) titration.

EXAMPLE 3

Following the general procedures of Example 2, but substituting about 100 mg. of lanthanide metal salt·HMPA catalyst complex for the metal salt·HMPA catalyst complexes of Example 2, there was obtained the following results:

TABLE II

| Catalyst Complex | 1 hour | | 2 hours | | 3 hours | |
|---|---|---|---|---|---|---|
| | Conv.* | ROOH$^a$ | Conv.* | ROOH$^a$ | Conv.* | ROOH$^a$ |
| HoCl$_3$ . HMPA | 5.9 | 6.7 | 12.5 | 13.7 | 19.2 | 19.6 |
| DyCl$_3$ . HMPA | 9.0 | 10.0 | 17.3 | 17.9 | 23.5 | 23.6 |
| ErCl$_3$ . HMPA | 9.4 | 9.8 | 17.6 | 16.3 | 23.7 | 23.3 |
| PrCl$_3$ . HMPA | 6.7 | 7.2 | 12.7 | 13.3 | — | — |
| SmCl$_3$ . HMPA | 9.9 | 9.8 | 17.3 | 16.2 | 22.5 | 21.4 |

*% Conversion by Oxygen Uptake
$^a$% ROOH by Titration

EXAMPLE 4

Following the general procedures of Example 2 but substituting 18.4 g. of sec.-butylnaphthalene for the cumene of that example, and 100 mg. of catalyst, sec.-butylnaphthalene hydroperoxide was obtained in accordance with the following tabulation.

TABLE III

| RUN | CATALYST | TEMP. | O$_2$ PRESSURE | % CONV. BY O$_2$ UPTAKE* | % ROOH |
|---|---|---|---|---|---|
| 1 | NdCl$_3$ . HMPA | 100° C | 1 Atmos. | 4 % | 1% (total) |
| 2 | TiCl$_4$ . HMPA | 105° C | 20 Atmos. | 2.2% | 9%* |

*After four hours.

EXAMPLE 5

Following the general procedures of Example 2, but substituting other secondary and tertiary alkylaromatics for cumene, the following results were obtained.

TABLE IV

| RUN | HMPA COMPLEXED WITH: | ALKYLAROMATIC | % CONVERSION BY O$_2$ UPTAKE | | | % ROOH | | |
|---|---|---|---|---|---|---|---|---|
| | | | 1 hr. | 2 hrs. | 3 hrs. | 1 hr. | 2 hrs. | 3 hrs. |
| 1 | NiCl$_2$ | Ethylbenzene | 1.6 | 3.9 | 4.6 | 2.4 | 4.4 | 5.1 |
| 2 | NdCl$_3$ | Ethylbenzene | 3.8 | 5.5 | — | 3.1 | 4.6 | — |
| 3 | NiCl$_2$ | N-Butylbenzene | 2.0 | 3.6 | — | 1.8 | 2.7 | — |
| 4 | NdCl$_3$ | N-Butylbenzene | 3.1 | 3.9 | — | 1.5 | 2.9 | — |
| 5 | NiCl$_2$ | Sec.-Butylbenzene | 0.7 | 2.1 | — | 0.6 | 2.7 | — |
| 6 | NdCl$_3$ | Sec.-Butylbenzene | 3.5 | 5.0 | — | 2.7 | 3.7 | — |

EXAMPLE 6

In an 80 ml. Morton flask equipped with a hollow-shafter stirrer and fitted with a Dry-Ice condenser was placed 18.4 g. (100 m moles) of -sec.-butylnaphthalene, 60 mg. of MnCl$_2$·2HMPA, and 0.2 cc of cumene by hydroperoxide. Oxygen was passed through the system with rapid stirring at the rate of 60 ml./minute. Within one hour a white solid deposited upon the cold condenser, and this solid was identified as actaldehyde by a comparison of the properties of its 2,4-di-nitrophenylhydrazone with an authentic sample.

EXAMPLE 7

Oxidation of Cumene under Oxygen Pressure with Metal-Complex Catalysis:

In a high pressure glass reaction tube were placed 12.0 g. (100 m moles) cumene; 0.2 cc cumene hydroperoxide; 0.1 g. DyCl$_3$·HMPA ($\sim$ 0.1 m mole) and a stirring bar. After pressuring the system to 300 psig with oxygen, the system was lowered into an equilibrated oil bath at 100° C and stirring commenced. After three hours the reaction was stopped. The total amount of oxygen consumed was 33 m moles (i.e., conversion=33%) and a sample showed 23.0% cumene hydroperoxide present by iodometric titration. The selectivity was therefore 70%.

Following the above general procedure, cumene was oxidized with the catalysts tabulated below under varying oxygen pressures. The following results are clear evidence of the fact that increased oxygen pressure significantly increases the rate of conversion of the cumene as compared with the rates of Example 2 which were carried out at atmospheric pressure.

TABLE V

EFFECT OF OXYGEN PRESSURE ON CUMENE AUTOXIDATION

| CATALYST | TEMP.° C | PRESSURE | mole % Oxygen Absorption 1 hr. | Final (time) | % ROOH* | % YIELD OF ROOH |
|---|---|---|---|---|---|---|
| $NdCl_2$ . HMPA | 90° | 200 psi | 17 | 21 (1½ hrs.) | 13.8 | 66 |
| $NdCl_2$ . HMPA | 100° | 285 psi | 19 | 26 (2 hrs.) | 20.1 | 77 |
| $ThO_2$ . HMPA | 100° | 200 psig | 9 | 15 (2 hrs.) | 12.4 | 83 |
| $TiCl_4$ . HMPA | 100° | 200 psig | — | 17 (4 hrs.) | 16.2 | 95 |

*by iodometric titration

EXAMPLE 8

The following data illustrates a preferred embodiment of this invention wherein the oxidation of cumene to form cumene hydroperoxide, using a variety of catalysts, was carried out in accordance with the procedures of Example 2, except that certain runs were accompanied by vigorous agitation, using a reciprocating disk type agitator instead of a conventional magnetic stirring barr:

TABLE VI

| Catalyst | Type of Agitation | Rate of Oxidation (mole %/hour) 1st hour | 2nd hour |
|---|---|---|---|
| None | Magnetic Stirring Bar | 0.2 | 0.7 |
|  | Reciprocating Disk Agitator | 1.8 | 4.4 |
| $NdCl_3$ . 3HMPA | Magnetic Stirring Bar | 4.3 | 8.5 |
|  | Reciprocating Disk Agitator | 17.2 | 25.4 |
| $CoCl_2$ . 2HMPA | Magnetic Stirring Bar | — | 7.6 |
|  | Reciprocating Disk Agitator | 14.9 | 18.4 |
| $McCl_2$ . 2HMPA | Magnetic Stirring Bar | 6.7 | 11.0 |
|  | Reciprocating Disk Agitator | 22.8 | 32.5 |

What is claimed is:

1. In the process for the catalytic oxidation of secondary or tertiary alkylaromatic hydrocarbons of the formula $$R_1-\underset{\underset{Ar}{|}}{\overset{\overset{R}{|}}{C}}-H$$

wherein R is lower alkyl; $R_1$ is lower alkyl or hydrogen; and Ar is an aromatic nucleus selected from the group consisting of phenyl and naphthyl, in the presence of air or oxygen at a temperature of from about 80 to 150° C to form a reaction mixture comprising the corresponding hydroperoxides, the improvement wherein the catalyst is of the formula $$MX_n(HAPA)_m$$

wherein HAPA is a hexaalkylphosphoramide, the alkyl moiety of which has from one to thirty carbon atoms; MX is metal salt wherein M is a transition metal cation of Group IB, IIB, IIIB, IVB, VB, VIB, VIIB, VIIIB or IIA of the Periodic Table and X is an inorganic anion of said metal salt; m is an integer of from 1 to 8; and n is an integer of from 1 to 4, wherein the ratio of said catalyst to said alkylaromatic hydrocarbon is from about 0.1 to 5.0 parts by weight of catalyst per 100 parts by weight of alkylaromatic hydrocarbon.

2. The process according to claim 1 wherein the alkyl moiety of the hexaalkylphosphoramide contains from 1 to 4 carbon atoms.

3. The process according to claim 1 wherein the reaction is carried out under vigorous agitation.

4. The process according to claim 1 wherein the oxygen is introduced at a rate of from about 0.5 to 300 liters per hour.

5. The process according to claim 1 wherein the ratio of catalyst to alkylaromatic substrate is in the range of from 0.5 to 1.5 parts by weight of catalyst per 100 parts of substrate.

6. The process according to claim 1 wherein the reaction is carried out at a temperature of from 50° to 150° C.

7. The process according to claim 1 wherein the reaction is carried out at a temperature of from 90° to 120° C.

8. The process according to claim 1 wherein the metal of the metal salt is of the lanthanide series.

9. The process according to claim 1 wherein the metal of the metal salt is of the actinide series.

10. The process according to claim 1 wherein the metal of the metal salt is a transition metal of the periodic table.

11. The process according to claim 1 wherein the metal of the metal salt is selected from the group consisting of nickel, titanium, thorium, lead, ferrous iron, bismuth, zinc and cerium.

12. The process according to claim 1 wherein the oxidation is carried out at an oxygen pressure of from 1 to 50 atmospheres.

13. The process according to claim 1 wherein the alkylaromatic compound is cumene, the catalyst is hexamethylphosphoramide and a lanthanide metal salt, and the product consists substantially of cumyl hydroperoxide.

14. The process according to claim 1 wherein the alkylaromatic compound is sec.-butylnaphthalene, the catalyst is hexamethylphosphoramide and a lanthanide metal salt, and the product is sec.-butylnaphthalene hydroperoxide.

15. The process according to claim 1 wherein the oxidation is carried out in the added presence of a hydroperoxide.

16. The process according to claim 1 wherein the anion of the metal salt is selected from the group consisting of bromides, chlorides, carbonates, nitrates, and perchlorates.

* * * * *